(12) United States Patent  (10) Patent No.: US 8,188,105 B2
Sakamoto et al.  (45) Date of Patent: May 29, 2012

(54) THERAPEUTIC AGENT FOR INFLAMMATORY BOWEL DISEASE COMPRISING URACIL DERIVATIVE AS ACTIVE INGREDIENT

(75) Inventors: Kazuki Sakamoto, Tokushima (JP); Fumio Nakagawa, Tokushima (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/682,599

(22) PCT Filed: Oct. 10, 2008

(86) PCT No.: PCT/JP2008/002861
§ 371 (c)(1), (2), (4) Date: Apr. 12, 2010

(87) PCT Pub. No.: WO2009/047904
PCT Pub. Date: Apr. 16, 2009

(65) Prior Publication Data
US 2010/0222372 A1  Sep. 2, 2010

(30) Foreign Application Priority Data

Oct. 11, 2007 (JP) .................. 2007-265339

(51) Int. Cl.
*A61K 31/513* (2006.01)
*A61K 31/506* (2006.01)
(52) U.S. Cl. ..................................... 514/274
(58) Field of Classification Search .................. None
See application file for complete search history.

(56) References Cited

U.S. PATENT DOCUMENTS

| | | | |
|---|---|---|---|
| 6,255,314 B1 | 7/2001 | Miyadera et al. | |
| 6,294,535 B1 | 9/2001 | Yano et al. | |
| 6,479,500 B1 | 11/2002 | Fukushima et al. | |

FOREIGN PATENT DOCUMENTS

| | | |
|---|---|---|
| EP | 0 884 051 | 12/1998 |
| EP | 0 906 760 | 4/1999 |
| EP | 1 080 726 | 3/2001 |
| JP | 2000 273044 | 10/2000 |
| WO | 96 30346 | 10/1996 |
| WO | 98 13045 | 4/1998 |
| WO | 2005/026131 | 3/2005 |
| WO | 2007 122812 | 11/2007 |

OTHER PUBLICATIONS

The Merck Manual, 17th edition (1999), pp. 302, 307.*
Saito, Shinsuke et al., "Expression of platelet-derived endothelial cell growth factor in inflammatory bowel disease", Journal of Gastroenterology, vol. 38, No. 3, pp. 229-237, (2003).
Targan R. Stephan et al., "A Short-Term Study of Chimeric Monoclonal Antibody cA2 to Tumor Necrosis Factor α for Crohn's Disease", The New England Journal of Medicine, vol. 337, No. 15, pp. 1029-1035, Oct. 9, 1997.
Rutgeerts, Paul et al., "Efficacy and Safety of Retreatment With Anti-Tumor Necrosis Factor Antibody (Infliximab) to Maintain Remission in Crohn's Disease", Gastroenterology, vol. 117, No. 4, pp. 761-769, Oct. 1999.
Supplementary European Search Report dated Jan. 31, 2012 as received in the corresponding European Patent Application No. 08838057.1-2123/2204175 (PCT/JP2008002861).

* cited by examiner

*Primary Examiner* — Phyllis G. Spivack
(74) *Attorney, Agent, or Firm* — Oblon, Spivak, McClelland, Maier & Neustadt, L.L.P.

(57) ABSTRACT

A therapeutic agent for inflammatory bowel disease contains, as an active ingredient, a uracil derivative or a pharmaceutically acceptable salt thereof, represented by formula (1) where the $R^1$ and $R^2$ groups are defined in the specification.

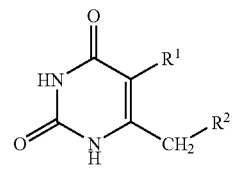

(1)

4 Claims, No Drawings

THERAPEUTIC AGENT FOR INFLAMMATORY BOWEL DISEASE COMPRISING URACIL DERIVATIVE AS ACTIVE INGREDIENT

CROSS-REFERENCE TO RELATED APPLICATIONS

This application is a 371 of PCT/JP08/002861 filed Oct. 10, 2008 and claims the benefit of JP 2007-265339.

FIELD OF THE INVENTION

The present invention relates to a therapeutic agent for an inflammatory bowel disease, comprising, as an active ingredient, a uracil derivative or a pharmaceutically acceptable salt thereof.

BACKGROUND OF THE INVENTION

Inflammatory bowel diseases (IBD) is a so-called intractable disease which its cause is unknown, and which involves chronic inflammation or ulcer of the mucosae of the large intestine and small intestine, persistent diarrhea and bloody stool for a long period of time, and recurrence of the symptoms. In Japan, IBD is designated as a "specified disease" (i.e., specified rare and intractable disease), and as part of the research projects for combating against such specified diseases, specified-disease recipient certificates are issued to patients suffering IBD. Two typical IBDs are Crohn's disease (CD) and ulcerative colitis (UC).

Crohn's disease, which is also called regional colitis, granulomatous ileitis, or ileocolitis, is a chronic inflammatory disease of intestinal wall and occurs at any site of the gastrointestinal tract. Ulcerative colitis is a chronic inflammatory disease involving inflammation of the large intestine resulting in ulcer formation, with symptoms of hemorrhagic diarrhea, severe abdominal pain, and attack thereof with fever. Although the patients of both diseases are more numerous in Europe and America than in Japan, the number of the patients has continuously increased in Japan. According to the statistics of 2001, there were about 73,000 ulcerative colitis patients, and about 21,000 Crohn's disease patients in Japan. Among 46 specific diseases, ulcerative colitis was first in the number of recipient certificate issues, and Crohn's disease was eighth.

Since the cause of inflammatory bowel disease, as described above, has not been identified, conventional therapeutic drugs for diarrhea and similar drugs are not effective to IBD. Instead, in the treatment of inflammatory bowel disease, an aminosalicylic acid drug (sulfasalazine, 5-aminosalicylic acid) and a corticosteroid drug have widely and conventionally been employed as drugs of first and second choice, respectively. In the case of severe IBD, an immunosuppressive agent (azathioprine, 6-mercaptopurine, etc.) or an anti-cytokine drug is also employed. As an aminosalicylic acid drug, sulfasalazine and 5-aminosalicylic acid are widely employed. However, about 50% of the patients who have taken an aminosalicylic acid drug complain of onset of gastrointestinal disorders such as nausea, vomiting, inappetence, and liver function disorders; and hematologic system disorders such as granulocytopenia, hemolytic anemia, and folic acid deficiency anemia. In addition, since aminosalicylic acid drugs have a salicylic acid skeleton, a patient having anaphylaxis to a salicylic drug may complain of adverse side effects, such as diarrhea, abdominal pain, rise in amylase level, and kidney disorders. Sulfasalazine causes adverse side effects such as male sterility and urine coloration, which impose large stress on the patients. Corticosteroid drugs cause various adverse side effects such as osteoporosis, growth disorders, secondary adrenal failure, impaired glucose tolerance, and hypertension, and are not effective for maintenance of remission in CD or UC, which are problematic. On the other hand, anti-cytokine therapy is a new therapy completely differing from conventional therapies. The first anti-cytokine drug is infliximab, which is a chimeric anti-human TNF-α monoclonal antibody. Infliximab is known to be effective for patients of medium to severe Crohn's disease having steroid resistance (Non-Patent Document 1), and for maintenance of remission in the target disease (Non-Patent Document 2). Known adverse side effects of infliximab include hypertension, chills, exanthem, fever, headache, and eczema. In addition, since infliximab is a chimeric antibody, it may be antigenic. In this case, acute super anaphylaxis may occur. Infliximab may cause infection which requires an antibiotic drug for the treatment thereof, and may exhibit carcinogenicity, which are also problems recognized recently.

Non-Patent Document 1: N. Engl. J. Med., vol. 337, p. 1029, 1997

Non-Patent Document 2: Gastroenterology, vol. 117, p. 761, 1999

SUMMARY OF THE INVENTION

Problems to be Solved by the Invention

An object of the present invention is to provide a novel therapeutic agent for inflammatory bowel disease.

Means for Solving the Problems

The present inventors have extensively studied therapeutic effects of a variety of compounds on inflammatory bowel disease employing a dextran-sulfate-sodium (DSS)-induced IBD model known as an inflammatory bowel disease model, and quite surprisingly, have found that uracil derivatives, which are known to have an effect of potentiating anti-tumor effect, a cancer-metastasis-inhibitory effect, and an effect of mitigating adverse side effects of an anti-cancer agent, exhibit an superior therapeutic effect on inflammatory bowel disease. The present invention has been accomplished on the basis of this finding.

Accordingly, the present invention provides a therapeutic agent for an inflammatory bowel disease containing a uracil derivative represented by the following formula (1) as an active ingredient:

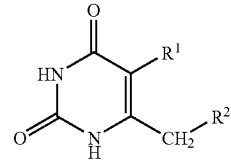

(1)

(wherein $R^1$ represents a chlorine atom, a bromine atom, an iodine atom, a cyano group, or a lower alkyl group; and $R^2$ represents a 4- to 8-membered heterocyclic group which is optionally substituted with a lower alkyl group, an imino group, a hydroxyl group, a hydroxymethyl group, a methanesulfonyloxy group, an amino group, or a nitro group and which has 1 to 3 nitrogen atoms; an amidinothio group in which a hydrogen atom bonded to the nitrogen atom is optionally substituted with a lower alkyl group; a guanidino group in which a hydrogen atom bonded to the nitrogen atom is optionally substituted with a lower alkyl group or with a cyano group; a lower alkylamidino group; an amino group in which a hydrogen atom bonded to the nitrogen atom is optionally substituted with a lower alkyl group; —CH$_2$N(R$^a$)R$^b$ group (wherein R$^a$ and R$^b$, which are identical to or different from each other, each represent a hydrogen atom or a lower alkyl group, or R$^a$ and R$^b$ may form a pyrrolidine ring with the nitrogen atom to which they are bonded); —NH—(CH$_2$)$_m$—Z group (wherein Z represents an amino group in which a hydrogen atom bonded to the nitrogen atom is optionally substituted with a lower alkyl group, or a cyano group; and m is an integer of 0 to 3); —NR$^c$(CH$_2$)$_n$—OH group (wherein R$^c$ represents a hydrogen atom or a lower alkyl group, and n is a natural number of 1 to 4); —X—Y group (wherein X represents S or NH; and Y represents a 2-imidazolin-2-yl, 2-imidazolyl, 1-methylimidazol-2-yl, 1,2,4-triazol-3-yl, 2-pyrimidyl, or 2-benzimidazolyl group which is optionally substituted with a lower alkyl group); or a ureido or thioureido group in which a hydrogen atom bonded to the nitrogen atom is optionally substituted with a lower alkyl group), with the proviso that 5-chloro-6-(2-iminopyrrolidin-1-yl)methyl-2,4(1H,3H)-pyrimidinedione is excluded, or a pharmaceutically acceptable salt thereof.

The present invention also provides use of a uracil derivative represented by formula (1) or a pharmaceutically acceptable salt thereof for producing a therapeutic agent for an inflammatory bowel disease.

The present invention also provides a method for treatment of an inflammatory bowel disease, characterized in that the method comprises administering, to a subject in need thereof, an effective amount of a uracil derivative represented by formula (1) or a pharmaceutically acceptable salt thereof.

Effects of the Invention

The present invention provides an effective and safe therapeutic agent for inflammatory bowel diseases including ulcerative colitis and Crohn's disease. The therapeutic effect of the uracil derivative represented by formula (1) or a pharmaceutically acceptable salt thereof on chronic inflammatory diseases, such as inflammatory bowel disease, is superior to a conventional therapeutic drug, such as an aminosalicylic acid drug or a corticosteroid drug. Such an effect can never be anticipated from their diarrhea inhibitory effect.

DETAILED DESCRIPTION OF THE INVENTION

The uracil derivatives represented by formula (1):

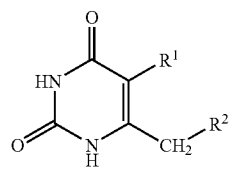

(1)

(wherein R$^1$ represents a chlorine atom, a bromine atom, an iodine atom, a cyano group, or a lower alkyl group; and R$^2$ represents a 4- to 8-membered heterocyclic group which is optionally substituted with a lower alkyl group, an imino group, a hydroxyl group, a hydroxymethyl group, a methanesulfonyloxy group, an amino group, or a nitro group and which has 1 to 3 nitrogen atoms; an amidinothio group in which a hydrogen atom bonded to the nitrogen atom is optionally substituted with a lower alkyl group; a guanidino group in which a hydrogen atom bonded to the nitrogen atom is optionally substituted with a lower alkyl group or with a cyano group; a lower alkylamidino group; an amino group in which a hydrogen atom bonded to the nitrogen atom is optionally substituted with a lower alkyl group; —CH$_2$N(R$^a$)R$^b$ group (wherein R$^a$ and R$^b$, which are identical to or different from each other, each represent a hydrogen atom or a lower alkyl group, or R$^a$ and R$^b$ may form a pyrrolidine ring with the nitrogen atom to which they are bonded); —NH—(CH$_2$)$_m$—Z group (wherein Z represents an amino group in which a hydrogen atom bonded to the nitrogen atom is optionally substituted with a lower alkyl group, or a cyano group; and m is an integer of 0 to 3); —NR$^c$(CH$_2$)$_n$—OH group (wherein R$^c$ represents a hydrogen atom or a lower alkyl group, and n is a natural number of 1 to 4); —X—Y group (wherein X represents S or NH; and Y represents a 2-imidazolin-2-yl, 2-imidazolyl, 1-methylimidazol-2-yl, 1,2,4-triazol-3-yl, 2-pyrimidyl, or 2-benzimidazolyl group which is optionally substituted with a lower alkyl group); or a ureido or thioureido group in which a hydrogen atom bonded to the nitrogen atom is optionally substituted with a lower alkyl group), with the proviso that 5-chloro-6-(2-iminopyrrolidin-1-yl)methyl-2,4(1H,3H)-pyrimidinedione is excluded, and a pharmaceutically acceptable salt thereof, which are employed as active ingredients in the drug of the present invention, are known compounds. There have been known the pharmacological effects of the compounds; i.e., an effect of potentiating anti-tumor effect (WO 96/30346), a cancer-metastasis-inhibitory effect (WO 98/13045), and an effect of mitigating adverse side effects of an anti-cancer agent (JP-A-2000-273044). However, effect of the compounds on inflammatory bowel disease has never been known.

In formula (1), the lower alkyl group represented by R$^1$ or R$^2$ is, for example, a C1 to C4 linear or branched alkyl group. Specific examples include methyl, ethyl, n-propyl, isopropyl, n-butyl, isobutyl, sec-butyl, and tert-butyl group. Of these, methyl group is preferred.

Examples of the a 4- to 8-membered heterocyclic group having 1 to 3 nitrogen atoms, represented by R$^2$, include 1-azetidinyl, 1-pyrrolidinyl, 2-pyrrolin-1-yl, 3-pyrrolin-1-yl, 1-pyrrolyl, 1-pyrazolidinyl, 2-pyrazolin-1-yl, 3-pyrazolin-1-yl, 4-pyrazolin-1-yl, 1-pyrazolyl, 1-imidazolidinyl, 2-imidazolin-1-yl, 3-imidazolin-1-yl, 4-imidazolin-1-yl, 1-imidazolyl, 1,2,3-triazol-1-yl, 1,2,4-triazol-1-yl, piperidino, 1-piperazyl, morpholino, 1-perhydroazepinyl, and 1-perhydroazocinyl group. The heterocycle of the heterocyclic group may have one or two substituents. Examples of such substituents include a lower alkyl group, an imino group, a hydroxyl group, a hydroxymethyl group, a methanesulfonyloxy group, an amino group, and a nitro group. Specific examples of the heterocyclic group which may have such a substituent include 1-azetidinyl, 1-pyrrolidinyl, 2,5-dimethylpyrrolidin-1-yl, 2-iminopyrrolidin-1-yl, 3-hydroxypyrrolidin-1-yl, 2-hydroxymethylpyrrolidin-1-yl, 3-methanesulfonyloxypyrrolidin-1-yl, 3-aminopyrrolidin-1-yl, 2-pyrrolin-1-yl, 3-pyrrolin-1-yl, 2-imino-3-pyrrolin-1-yl, 1-pyrrolyl, 1-pyrazolidinyl, 2-methylpyrazolidin-1-yl, 4-iminopyrazolidin-1-yl, 2-pyrazolin-1-yl, 3-pyrazolin-1-yl, 2-methyl-3-pyrazolin-1-yl, 5-imino-3-pyrazolin-1-yl, 4-pyrazolin-1-yl, 2-methyl-4-pyrazolin-1-yl, 3-imino-4-pyrazolin-1-yl, 1-pyrazolyl, 1-imidazolidinyl, 3-methylimidazolidin-1-yl, 2-iminoimidazolidin-1-yl, 2-imino-3-methylimidazolidin-1-yl, 2-imino-3-ethylimidazolidin-1-yl, 2-imino-3-isopropylimidazolidin-1-yl, 2-imidazolin-1-yl, 3-imidazolin -1-yl, 4-imidazolin-1-yl, 3-methyl-4-imidazolin-1-yl, 2-imino-4-imidazolin-1-yl, 2-imino-3-methyl-4-imidazolin -1-yl, 2-imino-3-ethyl-4-imidazolin-1-yl, 2-imino-3-isopropyl -4-imidazolin-1-yl, 1-imidazolyl, 2-methylimidazol-1-yl, 2-nitroimidazol -1-yl, 4-nitroimidazol-1-yl, 1,2,3-triazol-1-yl, 1,2,4-triazol-1-yl, 3-nitro-1,2,4-triazol-1-yl, piperidino, 1-piperazyl, 4-methylpiperazin-1-yl, morpholino, 1-perhydroazepinyl, and 1-perhydroazocinyl group. The preferred examples include 1-azetidinyl, 1-pyrrolidinyl, 2-iminopyrrolidin -1-yl, 2-iminoimidazolidin-1-yl, 2-imino-3-methylimidazolidin -1-yl, 2-imino-3-ethylimidazolidin-1-yl, 2-imino-3-isopropylimidazolidin-1-yl, 2-imidazolin-1-yl, 2-imino -3-methyl-4-imidazolin-1-yl, 2-imino-3-ethyl-4-imidazolin -1-yl, and 1-imidazolyl group.

In the amidinothio group in which a hydrogen atom bonded to the nitrogen atom of $R^2$ is optionally substituted with a lower alkyl group, 1 to 3 of the three hydrogen atoms each bonded to the nitrogen of the amidino group is optionally substituted with the aforementioned lower alkyl groups. Particularly preferred are an amidinothio group, an $N^1$-methylamidinothio group, and an $N^1,N^2$-dimethylamidinothio group.

In the guanidino group in which a hydrogen atom bonded to the nitrogen atom is optionally substituted with a lower alkyl group, or a cyano group, 1 to 4 of the four hydrogen atoms of the guanidino group is optionally substituted with the aforementioned lower alkyl group or a cyano group. Particularly preferred are a 1-guanidino group, a 1-methylguanidino group, a 3-methylguanidino group, a 2,3-dimethylguanidino group, and a 2-cyano-3-methylguanidino group.

The lower alkylamidino group is a group wherein the aforementioned lower alkyl group is bonded to an amidino group. Among such groups, an acetamidino group is preferred.

In the amino group in which a hydrogen atom bonded to the nitrogen atom is optionally substituted with a lower alkyl group, 1 or 2 of the two hydrogen atoms of the amino group is optionally substituted with the aforementioned lower alkyl group. Among such groups, an amino group, an N-methylamino group, an N,N-dimethylamino group, an N-ethylamino group, an N,N-diethylamino group, an N-propylamino group, and an N-isopropylamino group are preferred.

Among —$CH_2N(R^a)R^b$ groups, preferred are an N-methylaminomethyl group, an N,N-dimethylaminomethyl group, and a 1-pyrrolidinylmethyl group.

Among —NH—$(CH_2)_m$—Z groups, preferred are an N,N-dimethylhydrazino group, an N-(2-aminoethyl)amino group, an N-(2-(N,N-dimethyl)aminoethyl)amino group, an N-(3-aminopropyl)amino group, and an N-(2-cyanoethyl)amino group.

Among —$NR^c(CH_2)_n$—OH groups, preferred are an N-(2-hydroxyethyl)-N-methylamino group, an N-(3-hydroxypropyl)amino group, and an N-(4-hydroxybutyl)amino group.

Among —X—Y groups, preferred are a 2-imidazoline-2-thio group, a 2-imidazolin-2-amino group, an imidazol-2-thio group, a 1-methylimidazole-2-thio group, a 1,2,4-triazole-3-thio group, a pyrimidine-2-thio group, and a benzimidazole-2-thio group.

Among the ureido or thioureido groups in which a hydrogen atom bonded to the nitrogen atom is optionally substituted with a lower alkyl group, a ureido group and a 3-methylthioureido group are preferred.

In formula (1), $R^1$ is preferably a chlorine atom or a bromine atom.

In formula (1), the group $R^2$ is preferably a 4- to 8-membered heterocyclic group which is optionally substituted with a lower alkyl group, an imino group, a hydroxyl group, a hydroxymethyl group, a methanesulfonyloxy group, an amino group, or a nitro group and which has 1 to 3 nitrogen atoms; an amino group in which a hydrogen atom bonded to the nitrogen atom is optionally substituted with a lower alkyl group; —$NR^c(CH_2)_n$—OH group (wherein $R^c$ represents a hydrogen atom or a lower alkyl group, and n is a natural number of 1 to 4); or —X—Y group (wherein X represents S or NH; and Y represents a 2-imidazolin-2-yl, 2-imidazolyl, 1-methylimidazol -2-yl, 1,2,4-triazol-3-yl, 2-pyrimidyl, or 2-benzimidazolyl group which is optionally substituted with a lower alkyl group). The group $R^2$ is more preferably a 4- to 8-membered heterocyclic group which is optionally substituted with an imino group and which has 1 to 3 nitrogen atoms; an amino group in which a hydrogen atom bonded to the nitrogen atom is optionally substituted with a lower alkyl group; —$NR^c(CH_2)_n$—OH group (wherein $R^c$ represents a lower alkyl group, and n is a natural number of 1 to 4); or a 1,2,4-triazole-3-thio group. The group $R^2$ is particularly preferably a 1-pyrrolidinyl group, a 1-imidazolidinyl group which is optionally substituted with an imino group, a lower alkylamino group, —$NR^c(CH_2)_2$—OH group (wherein $R^c$ represents a lower alkyl group), or a 1,2,4-triazole-3-thio group.

Specific examples of preferred groups $R^2$ include 1-azetidinyl, 1-pyrrolidinyl, 2-iminopyrrolidin-1-yl, 2-iminoimidazolidin -1-yl, 2-imino-3-methylimidazolidin-1-yl, 2-imino -3-ethylimidazolidin-1-yl, 2-imino-3-isopropylimidazolidin -1-yl, 2-imidazolin-1-yl, 2-imino-3-methyl -4-imidazolin-1-yl, 2-imino-3-ethyl-4-imidazolin-1-yl, 1-imidazolyl, amidinothio, W-methylamidinothio, $N^1,N^2$-dimethylamidinothio, 1-guanidino, 1-methylguanidino, 3-methylguanidino, 2,3-dimethylguanidino, and acetamidino group. The group $R^2$ is particularly preferably a 1-pyrrolidinyl group, a 2-iminoimidazolidin-1-yl group, a methylamino group, an N-(2-hydroxyethyl)-N-methylamino group, or a 1,2,4-triazole -3-thio group.

In the uracil derivative represented by formula (1), preferably, $R^1$ is a chlorine atom or a bromine atom; and $R^2$ is a 1-pyrrolidinyl group, a 2-iminoimidazolidin-1-yl group, a methylamino group, an N-(2-hydroxyethyl)-N-methylamino group, or a 1,2,4-triazole-3-thio group.

The uracil derivative represented by formula (1) is not particularly limited, the salt is preferably an acid addition salt and/or a basic salt produced by use of a pharmaceutically acceptable acid or basic compound. Examples of the acid addition salt include salts with an inorganic acid such as hydrochloric acid, sulfuric acid, phosphoric acid, or hydrobromic acid; and salts with an organic acid such as oxalic acid, maleic acid, fumaric acid, malic acid, tartaric acid, citric acid, benzoic acid, acetic acid, p-toluenesulfonic acid, or methanesulfonic acid. Of these, hydrochloric acid salts and p-toluenesulfonic acid salts are preferred. Examples of the basic salt include salts with an alkali metal or an alkaline earth metal such as sodium, potassium, magnesium, or calcium; and salts with an amine such as ammonia, methylamine, dimethylamine, piperidine, cyclohexylamine, or triethylamine.

Specific examples particularly preferred uracil derivatives (1) and salts thereof include the following:

5-chloro-6-(methylaminomethyl)uracil (compound (1)), 5-chloro -6-(1-pyrrolidinylmethyl)uracil (compound (2)), 5-chloro -6-((N-(2-hydroxyethyl)-N-methylamino)methyl) uracil (compound (3)), 5-chloro-6-(1,2,4-triazole-3-thiomethyl)uracil hydrochloride salt (compound (4)), 5-chloro -6-(1-(2-iminoimidazolidinyl)methyl)uracil (compound (5)), and 5-bromo-6-(1-pyrrolidinylmethyl)uracil (compound (6)).

The uracil derivatives (1) of the present invention may be produced from a variety of compounds as sources through a method, for example, a method disclosed in WO96/30346.

As described in the Example hereinbelow, the uracil derivative (1) or a salt thereof has a remarkably superior anti-inflammatory effect on a DSS-induced IBD model known as an inflammatory bowel disease model. In addition, the uracil derivative (1) or a salt thereof has high safety. In consideration that conventional therapeutic agents for inflammatory bowel disease cause various problematic adverse side effects, the uracil derivative (1) or a salt thereof serves as a novel, useful therapeutic agent for inflammatory bowel disease, which has never existed.

Meanwhile, the uracil derivative (1) and a salt thereof are known to be thymidine phosphorylase inhibitors. However, thymidine phosphorylase is hardly expressed in the gastrointestinal tract of rodents such as mice employed in the Example. Therefore, it is difficult to conclude that the therapeutic effect on inflammatory bowel disease can be provided exclusively through the thymidine phosphorylase inhibitory effect of the uracil derivative (1). Although an anti-cancer agent is also known to have a diarrhea inhibitory effect, the disclosed effect is attributed to a cell injury inhibitory effect provided by the anti-cancer agent, therefore, the therapeutic effect on chronic inflammatory disease of the present invention can never be anticipated from the above background art. In addition, thymidine phosphorylase is known to induce angiogenesis by a PD-ECGF activity. It is reported that a thymidine phosphorylase inhibitor is employed as a cancer-metastasis inhibitor based on the angiogenesis inhibitory effect. However, utility of such a thymidine phosphorylase inhibitor as a therapeutic agent for inflammatory bowel disease is unknown.

The target disease of the present invention is inflammatory bowel disease. Examples thereof include Crohn's disease, ulcerative colitis, collagenous colitis, lymphocytic colitis, and colitis after urinary diversion. Particularly, the target disease of the invention is Crohn's disease or ulcerative colitis.

The uracil derivative (1) or a salt thereof itself may be formulated into a variety of unit dosage forms and may be administrated.

When the drug of the present invention is used as a therapeutic agent for IBD of mammal including human, a variety of pharmaceutical dosage forms may be employed in accordance with the purpose of the treatment. Specifically, examples thereof include oral preparations such as tablets, coated tablets, pills, powders, granules, capsules, solutions, suspensions, and emulsions; and parenteral preparations such as injections and suppositories. The dosage forms of the agent may be prepared by use of, for example, a pharmaceutically acceptable carrier through a conventional drug preparation method generally known in the art. In forming tablets, examples of the carrier which may be employed in the invention include fillers such as lactose, sucrose, sodium chloride, glucose, urea, starch, calcium carbonate, kaolin, crystalline cellulose, and silicic acid; binders such as water, ethanol, propanol, corn starch, simple syrup, glucose solution, starch solution, gelatin solution, carboxymethyl cellulose, shellac, methyl cellulose, hydroxypropyl cellulose, hydroxypropylmethyl cellulose, potassium phosphate, and polyvinylpyrrolidone; disintegrating agents such as dry starch, sodium alginate, agar powder, laminaran powder, sodium bicarbonate, calcium carbonate, polyoxyethylene sorbitan fatty acid esters, sodium lauryl sulfate, stearic acid monoglyceride, and lactose; disintegration inhibitors such as sucrose, stearic acid, cacao butter, and hydrogenated oil; absorption-accelerating agents such as quaternary ammonium salts and sodium lauryl sulfate; humectants such as glycerol and starch; adsorbents such as starch, lactose, kaolin, bentonite, and colloidal silica; and lubricants such as purified talc, stearic acid salts, boric acid powder, and polyethylene glycol. If required, tablets may be made into coated tablets using usual coatings, such as sugar-coated tablets, gelatin-coated tablets, enteric coated tablets, film-coated tablets, double-layer tablets, and multi-layer tablets. In forming pills, examples of the carriers to be employed include fillers such as glucose, lactose, starch, cacao butter, hydrogenated vegetable oil, kaolin, and talc; binders such as powdered acacia, powdered tragacanth, gelatin, and ethanol; and disintegrating agents such as powdered laminaran and powdered agar. Capsules are prepared through a routine method by mixing an active ingredient with the aforementioned various carriers and filling appropriate capsules such as hard gelatin capsules or soft capsules with the mixture. In forming oral liquid preparations (e.g., liquid preparations for internal use, syrups, and elixirs) may be produced through a routine method by use of a flavoring agent, a buffer, a stabilizer, a corrigent, etc. Examples of the flavoring agent include sucrose, orange peel, citric acid, and tartaric acid, and examples of the buffer include sodium citrate. Examples of the stabilizer include tragacanth, acacia, and gelatin. In forming suppositories, examples of the carrier to be employed include polyethylene glycol, cacao butter, higher alcohol, higher alcohol esters, gelatin, and semi-synthetic glyceride. In forming injections, injection liquids, injection emulsions, and injection suspensions are sterilized, and are preferably isotonic to blood. Examples of the diluent to be used in forming injections include water, aqueous lactic acid, ethyl alcohol, propylene glycol, macrogol, ethoxylated isostearyl alcohol, polyoxyethylenated isostearyl alcohol, and polyoxyethylene sorbitan fatty acid esters. In the case of injection preparation, the pharmaceutical preparation may contain sodium chloride, glucose, or glycerol in an amount sufficient for preparing isotonic solution. The preparation may also contain generally employed other additives such as a solubilizing agent, a buffer, and a soothing agent. If required, the aforementioned preparation may further contain a colorant, a preservative, a aromatic, a flavor, a sweetener, etc. and other pharmaceutical products. The amount of the uracil derivative (1) or a pharmaceutically acceptable salt thereof contained in the drug preparation of the present invention is not particularly limited, and the amount may be appropriately selected. Generally, the amount of them is preferably about 0.01 to about 70 wt. % of the drug preparations.

The method of administering the pharmaceutical agent of the present invention is not particularly limited, and the method is appropriately selected depending on, for example, the dosage form, the age, sex, or other conditions of a patient, or the severity of symptoms of a patient. For example, tablets, pills, powders, granules, capsules, solutions, suspensions, and emulsions are orally administered. Injections alone or mixtures thereof with a general injection liquid such as glucose or amino acid are intravenously administered. If required, they are administered alone intraarterially, intramuscularly, intracutaneously, subcutaneously, or intraperitoneally. Suppositories are used through rectal administration.

The dose of the active ingredient of the pharmaceutical agent of the present invention is appropriately selected depending on, for example, the dosage form, the age, sex, or other conditions of a patient, or the severity of symptoms of a patient. The dose of the uracil derivative (1) or a salt thereof is generally about 0.01 to about 1,000 mg/kg/day, preferably about 0.1 to about 100 mg/kg/day. The drug preparation of the present invention may be administered once or 2 to 4 times a day.

EXAMPLES

The present invention is described in more detail by way of example, which should not be construed as limiting the invention thereto.

Formulation Example 1

| | |
|---|---|
| Compound (1) | 25.0 mg |
| Lactose | 8.0 mg |
| Crystalline cellulose | 4.0 mg |
| Mg stearate | 1.0 mg |
| Talc | 1.0 mg |
| Cornstarch | 3.5 mg |
| Hydroxypropylmethyl cellulose | 2.5 mg |
| Total/tablet | 45.0 mg |

These ingredients were mixed through a routine method at the above composition, to thereby prepare tablets.

Formulation Example 2

| | |
|---|---|
| Compound (2) | 50.0 mg |
| Lactose | 85.0 mg |
| Cornstarch | 100.0 mg |
| Hydroxypropylmethyl cellulose | 3.0 mg |
| Total/packet | 238.0 mg |

These ingredients were mixed through a routine method at the above composition, to thereby prepare granules.

Formulation Example 3

| | |
|---|---|
| Compound (3) | 50.0 mg |
| Lactose | 24.0 mg |
| Crystalline cellulose | 13.0 mg |
| Mg stearate | 1.0 mg |
| Total/capsule | 45.0 mg |

These ingredients were mixed through a routine method at the above composition, to thereby prepare capsules.

Formulation Example 4

Injection

| | |
|---|---|
| Compound (4) | 50.0 mg |
| Distilled water for injection use | quant. suff. |
| Total/ample | 5 mL |

The compound was dissolved in water through a routine method at the above ratio (per ampoule), to thereby prepare injections.

Formulation Example 5

Suppository

| | |
|---|---|
| Compound (5) | 100.0 mg |
| Witepsol W-35 (registered trademark, Dynamit-Novel) | 1,400.0 mg |
| Total/suppository | 1,500.0 mg |

These ingredients were mixed through a routine method at the above proportion (per suppository), to thereby prepare suppositories.

Example 1

Effect on Improvement of Pathological Conditions in DSS-Induced IBD Model

This test was performed in accordance with the method described in PEDIATRIC RESEARCH, Vol. 53, No. 1, 143-147, 2003. Specifically, on day 0, mice (12-week-old, C57BL/6N Jcl, CLEA Japan, Inc.) were grouped such that the groups had an equivalent mean body weight (n=6). Dextran sulfate sodium (hereinafter abbreviated as "DSS," product of Wako Pure Chemical Industries, Ltd.) was dissolved in purified water to 2% w/v, and the solution was fed ad libitum to the mice for seven days through a liquid-feed bottle (day 1 to day 7), to thereby establish ulcerative colitis models. The test groups included a drug-non-administration group (control), and a uracil derivative (1)-administration (30 mg/kg/day) group. A non-treatment group was provided through feeding purified water instead of 2% aqueous DSS solution. The drug was administered for eight days from one day before start of feeding 2% aqueous DSS solution (i.e., from day 0 to day 7). The improvement effect was determined on the day following the final drug administration day (on day 8) by counting occurrence of abnormal stools (loose stool, diarrhea, and visual observation of presence of blood in stool). The effect was also evaluated on the basis of DAI scores shown in Table 1.

TABLE 1

DAI scores

| Score | Body weight loss (%) | Stool hardness | Fecal occult blood |
|---|---|---|---|
| 0 | no | normal | no |
| 1 | 1 to 5 | | |
| 2 | 5 to 10 | loose | positive |
| 3 | 10 to 20 | | |
| 4 | >20 | diarrhea | blood flow |

1) Results

In the control group, abnormal stool was observed in all tested mice on the day of evaluation. In contrast, as shown in Table 2, occurrence of abnormal stool was reduced in mice to which the uracil derivative (1) had been administered. Therefore, administration of the uracil derivative (1) was found to mitigate colitis induced by DSS.

TABLE 2

Effect of uracil derivatives on DSS-induced mouse colitis
(Evaluation based on occurrence of abnormal stool)

| Compound No. | Structure | Abnormal stool occurrence |
|---|---|---|
| | Non-treatment | 0 |
| | Control | 6 |
| 1 | 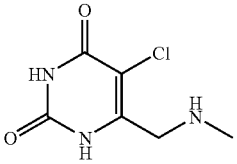 | 4 |
| 2 | 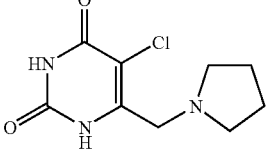 | 3 |
| 3 | 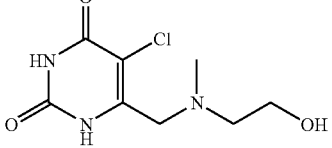 | 3 |
| 4 | 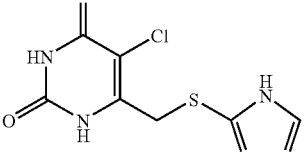 | 0 |
| 5 | 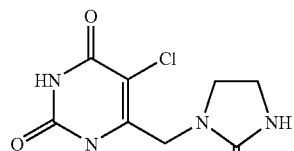 | 0 |
| 6 | 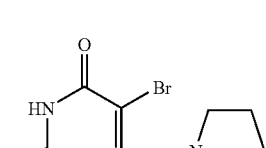 | 2 |

The effect on ameliorating colitis was further evaluated on the basis of DAI scores. As shown in Table 3, compounds listed in Table 3 were found to significantly improve DAI score.

TABLE 3

Effect of uracil derivatives on DSS-induced colitis mouse model

| Compound No. | Structure | DAI Score (MEANS ± SD) |
|---|---|---|
| | Control | 5.3 ± 2.1 |
| 4 | 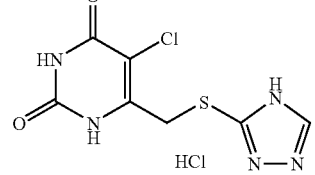 | 0.22 ± 0.27** |
| 5 | 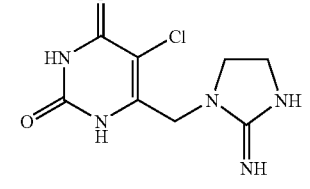 | 0.28 ± 0.25* |
| 6 | 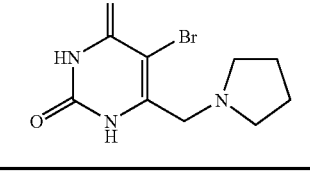 | 0.22 ± 0.27** |

The test has revealed that the uracil derivative (1) serves as a useful therapeutic agent for inflammatory bowel disease.

The invention claimed is:

1. A method for treatment of an inflammatory bowel disease, wherein the method comprises administering an effective amount of a uracil derivative represented by formula (1) to a subject in need thereof:

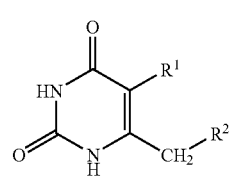

(1)

$R^1$ is a chlorine atom or a bromine atom, and $R^2$ is a 1-pyrrolidinyl group, a 1-imidazolidinyl group which is optionally substituted with an imino group, a lower alkylamino group, —$NR^c(CH_2)_2$—OH group, or a 1,2,4-triazole-3-thio group, wherein $R^c$ represents a lower alkyl group, or a pharmaceutically acceptable salt thereof.

2. The method according to claim 1, wherein the inflammatory bowel disease is ulcerative colitis or Crohn's disease.

3. The method according to claim 1, wherein the uracil derivative or a pharmaceutically acceptable salt thereof is

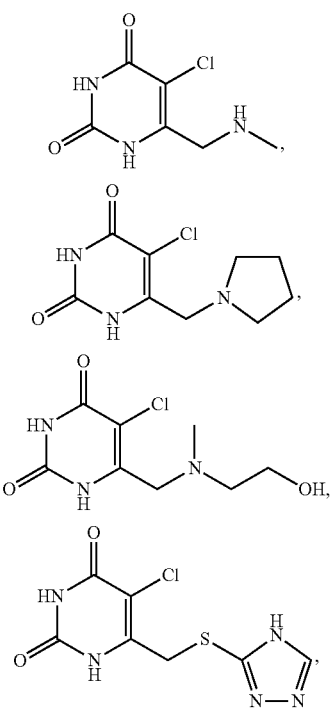
a hydrochloride of
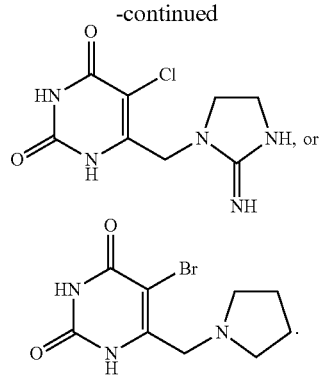
4. The method according to claim 1, wherein the pharmaceutiucally acceptable salt of the uracil derivative is a hydrochloride of
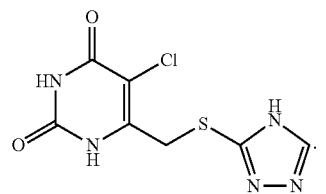
* * * * *